United States Patent [19]

Vanderpool

[11] 4,321,413
[45] Mar. 23, 1982

[54] PRODUCTION OF ETHYLENE GLYCOL DIALKYL ETHERS USING DIALKYL ETHERS

[75] Inventor: Steven H. Vanderpool, Austin, Tex.

[73] Assignee: Texaco Inc., White Plains, N.Y.

[21] Appl. No.: 229,821

[22] Filed: Jan. 30, 1981

[51] Int. Cl.³ .............................................. C07C 41/41
[52] U.S. Cl. .................................................... 568/672
[58] Field of Search ........................................ 568/672

[56] References Cited

FOREIGN PATENT DOCUMENTS 2917085 11/1979 Fed. Rep. of Germany .

OTHER PUBLICATIONS

"Catalytic Uses of Nafion ® Perfluorosulfonic Acid Products," Polymer Products Dept. E. I. du Pont de Nemours & Co. Inc., Research Disclosure, pub. by Industrial Opportunities, Ltd., Hampshire, Eng. Jul. 1980, paragraph 19515, pp. 270–271.

Vaughan, D. J.," 'Nafion', an Electrochemical Traffic Controller," E. I. du Pont de Nemours & Co. Inc., Technical Bulletin.

Primary Examiner—Howard T. Mars
Attorney, Agent, or Firm—Carl G. Ries; Jack H. Park; David L. Mossman

[57] ABSTRACT

A method for the production of ethylene glycol dialkyl ethers from dialkyl ethers and ethylene glycol monoalkyl ethers by means of passing these reactants over a heterogeneous anionic ion exchange resin catalyst is described. The reaction may be conducted at temperatures ranging from about 100° to about 250° C. and at pressures ranging from about 50 to about 500 psig. This method avoids some of the separation difficulties associated with preparing these compounds by prior wet chemistry methods.

9 Claims, No Drawings

PRODUCTION OF ETHYLENE GLYCOL DIALKYL ETHERS USING DIALKYL ETHERS

A related application, Ser. No. 229,825 dealing with the production of ethylene glycol dialkyl ethers from alcohols and ethylene glycol monoalkyl ethers has been filed of even date.

BACKGROUND OF THE INVENTION

1. Field of the Invention

This invention relates to methods for the production of ethylene glycol dialkyl ethers and more particularly relates to the production of ethylene glycol dialkyl ethers from reacting dialkyl ethers with ethylene glycol monoalkyl ethers in the presence of a heterogeneous anionic ion exchange resin catalyst.

2. Description of the Prior Art

Ethylene glycol dialkyl ethers, also known as glymes, have traditionally been very difficult to make by wet chemical procedures. Part of the difficulty with prior art methods has been in separating the glymes from the homogeneous product mixture that may contain a catalyst that is also desirable to recover. Glymes have utility in functional fluids such as transmission fluids and paint solvent formulations.

The compound designated as glyme (ethylene glycol dimethyl ether), which gives its name to the entire family of related compounds, has been prepared by a variety of methods. Russian Pat. No. 162,523 discloses how glyme may be made by reacting $(CH_3)_2SO_4$ with sodium glycolate in an aqueous alcoholic mixture having a pH in the range from 7 to 8. Glyme may also be produced by reacting $CH_3OCH_2CH_2Cl$ with $MeO^-$ ions in a methanolic solution at 40° to 180° C. according to French Pat. No. 1,567,133. Another method for making glyme in 14% yield along with ethylene glycol monomethyl ether in 17% yield is described by M. Pormale, et al. in Zh. Organ. Khim. 1 (10), 175862 (1965) in which ethylene glycol and $CH_2N_2$ are reacted at 20° C.

T. Koyano, et al. reveal how ethylene dichloride may be reacted with methanol at 200° C. in the presence of $Mg(OH)_2$ or $Zn(OH)_2$, which serve as HCl scavengers, to give glyme in 85% conversion and 80% selectivity, Kogyo Kagaku Zasshi, 1971, 74(2), 203-7. U.S. Pat. No. 3,699,174 also reacts ethylene dichloride with methanol at 200° C. for about six hours in the presence of ZnO to give glyme in 65.9% yield. Ethylene dichloride is again reacted with methanol for six hours from 150° to 350° C. as described in Japanese patent No. 75-09,764, this time in the presence of alkali earth metals manganese, iron or cobalt or their hydroxides or alkali earth alcoholates.

Ethylene is reacted with methanol and iodine in the presence of oxygen at 140° to 160° C. to produce mostly glyme but some methyl iodide and $CH_3OCH_2CH_2I$ as described in Japanese Pat. No. 75-07,578. German Offenlegungsschrift No. 2,434,057 reveals that 89% glyme yield may be obtained by reacting $(CH_3OCH_2CH_2O)_2CH_2$ at 160° C. over a nickel, cobalt or copper catalyst in the presence of hydrogen.

Other methods have made glyme in poor yields from alcohols and alkylene oxides. For example, M. R. Leanov and I. A. Korshunov produce mostly ethylene glycol monomethyl ether along with 5% glyme by reacting methanol with ethylene oxide at 200° C. and 6 to 32 atm, Tr. po Khim. i Khim. Teknol. 1964 (3), 51520. Japanese Pat. No. 78-37,607 discloses that $C_2C_4$ alkylene oxides reacted with various alcohols and $(CH_3)_2CHOH$ at 120° C. can produce ethylene glycol monomethyl ether and related products along with a small amount of glyme. It has further been discovered that the oxyalkylation of hydroxyl compounds with alkylene oxides in the presence of a sulfonated perfluorocarbon polymer resin catalyst give primarily the mono-oxyalkylated derivative, German Offlegungsschrift No. 2,917,805.

Given the low glyme yields and separation problems associated with the homogeneous systems of the prior methods, it is an object of this invention to provide a method for the production of glymes in high yield via a system using a heterogeneous catalyst that minimizes difficulties with the separation procedures.

SUMMARY OF THE INVENTION

The invention is a method for the production of ethylene glycol dialkyl ethers of the formula $ROCH_2CH_2OR$, where R is a lower alkyl radical, comprising reacting a dialkyl ether of the formula ROR with an ethylene glycol monoalkyl ether of the formula $ROCH_2CH_2OH$, where R is defined as above, over a heterogeneous anionic ion exchange resin catalyst.

DESCRIPTION OF THE PREFERRED EMBODIMENTS

Generally, the invention consists of passing a reaction mixture of a dialkyl ether and an ethylene glycol monoalkyl ether over a heterogeneous ionexchange resin catalyst at an elevated temperature. The dialkyl ether may be defined as ROR and the ethylene glycol monoalkyl ether may be defined as $ROCH_2CH_2OH$ where R in both cases represents lower alkyl. The instant disclosure uses examples where the R group is the same for both the dialkyl ether and the monoalkyl ether, which produces a symmetrical product ethylene glycol dialkyl ether. However, there appears to be no reason why the substituent alkyl groups could not be different from each other resulting in an asymmetrical product dialkyl ether.

The reactants used in the examples of this disclosure are dimethyl ether, diethyl ether, ethylene glycol monomethyl ether, and ethylene glycol monoethyl ether. Ethylene glycol monomethyl ether is sold under the name JEFFERSOL® EM ether and ethylene glycol monoethyl ether is sold under the name JEFFERSOL EE ether, both manufactured by Texaco Chemical Company. One skilled in the art would expect other lower alkyl substituents homologous with methyl and ethyl to be useful in the method of this invention. Generally, the mole ratio of the dialkyl ether to the ethylene glycol monoalkyl ether is preferred to be in the range of from 1:1 to 10:1.

The resin catalyst useful in this invention preferably is an "acid" or anionic ion exchange resin that would be a solid under the conditions of the inventive method. Especially preferred are sulfonic acid resins and phosphonic acid resins. Examples of sulfonic acid resin catalysts are LEWATIT® resins manufactured by Diamond Shamrock Chemical Company, AMBERLYST® 15 and AMBERLYST XN-1010 resins made by Rohm and Haas Co., and NAFION® perfluorosulfonic acid resin catalyst manufactured by E. I. duPont de Nemours & Co. An example of a phosphonic acid resin is DUOLITE® ES-473 produced by Diamond Alkali Co. The catalysts used in the examples herein have generally been shown to have a catalyst life of about 130 hours at 180° to 200° C. It is anticipated that a mixture of acid resins would also be useful in the method of this invention.

The examples disclosed herein illustrate that the method of the invention gives excellent results under a variety of conditions. The temperature range for this method is preferably 100° to 250° C. and is especially preferred to be in the range of about 125° to about 300° C. Pressures are preferably in the range upward from of 50 psig and are especially preferred to be in the range of about 100 to about 500 psig. Space velocities of the reactants typically range from about 0.5 to about 3.5 gram reactant mixture/gram catalyst/hour.

The method of this invention is further illustrated by the following examples. The examples using ethylene glycol monomethyl ether as a reactant employ JEFFERSOL EM ether and the ethylene glycol monoethyl ether used is JEFFERSOL EE ether, both manufactured by Texaco Chemical Company.

In the examples presented herein, a feed of the indicated molar ratio was charged to a supply tank and kept under 100 psig pressure. The feed was then pumped across 25 cc of catalyst at the conditions specified in Tables I and II.

The catalyst was comprised of 33 wt. % NAFION 511 resin and 67 wt. % DUOLITE ES-473 resin. In this manner, the DUOLITE resin allowed flow between the NAFION particles, thereby preventing plugging of the reactor. An inert or active material could be used so long as it allows flow at the reaction temperature and pressure. The purpose of such material is to act as a diluent to alleviate the packing of the soft NAFION resin. The liquid product was collected and analyzed by gas chromatography.

TABLE I[a]

ETHYLENE GLYCOL DIMETHYL ETHER (GLYME)

| Ex. | Temp, °C. | Press, psig | Space Velocity, hr.$^{-1}$ | Conversion to J-EM | % Selectivity[b] Glyme | Dioxane | J-DM | Diglyme |
|---|---|---|---|---|---|---|---|---|
| 1 | 180 | 150 | 3.2 | 55.4 | 62.4 | 20.0 | 1.0 | 16.5 |
| 2 | 180 | 200 | 3.2 | 55.9 | 65.5 | 15.3 | — | 19.2 |
| 3 | 180 | 250 | 3.2 | 52.1 | 66.7 | 9.3 | 6.1 | 17.4 |
| 4 | 180 | 150 | .64 | 80.2 | 52.5 | 41.3 | — | 6.2 |

[a]JEFFERSOL EM: Dimethyl ether ratio of 1:2 (molar ratio)
[b]Selectivity on a lights-free basis

TABLE II

ETHYLENE GLYCOL DIETHYL ETHER (ETHYL GLYME)

| Ex. | Temp, °C. | Press, psig | Velocity, hr.$^{-1}$ | J-EE/Et$_2$O ratio[a] | % Conversion to J-EE | % Selectivity[b] Ethyl Glyme | Dioxane | Heavies |
|---|---|---|---|---|---|---|---|---|
| 5 | 170 | 150 | .64 | 1:1 | 70.0 | 77.8 | 3.2 | 19.0 |
| 6 | 180 | 150 | .64 | 1:1 | 81.7 | 75.0 | 12.3 | 12.7 |
| 7 | 180 | 200 | .64 | 1:1 | 78.1 | 77.7 | 5.0 | 17.3 |
| 8 | 180 | 250 | .64 | 1:1 | 74.4 | 81.8 | 2.4 | 15.8 |
| 9 | 190 | 150 | .64 | 1:1 | 85.3 | 61.3 | 36.4 | 2.3 |
| 10 | 170 | 150 | .64 | 1:2 | 82.0 | 79.5 | 7.9 | 12.5 |
| 11 | 180 | 150 | .64 | 1:2 | 84.3 | 75.1 | 21.3 | 3.6 |
| 12 | 180 | 200 | .64 | 1:2 | 86.2 | 79.1 | 13.6 | 7.4 |
| 13 | 180 | 250 | .64 | 1:2 | 85.6 | 81.4 | 6.0 | 12.6 |
| 14 | 180 | 300 | .64 | 1:2 | 83.5 | 85.8 | 2.7 | 11.5 |
| 15 | 190 | 150 | .64 | 1:2 | 87.1 | 73.4 | 23.7 | 2.9 |
| 16 | 170 | 150 | 3.2 | 1:2 | 30.9 | 78.4 | c | 21.6 |
| 17 | 180 | 150 | 3.2 | 1:2 | 44.1 | 80.5 | c | 19.5 |
| 18 | 180 | 200 | 3.2 | 1:2 | 48.5 | 81.3 | c | 18.7 |
| 19 | 180 | 250 | 3.2 | 1:2 | 49.5 | 83.7 | c | 16.3 |
| 20 | 180 | 300 | 3.2 | 1:2 | 49.2 | 86.2 | c | 13.8 |
| 21 | 190 | 150 | 3.2 | 1:2 | 68.0 | 76.1 | 8.1 | 15.7 |
| 22 | 190 | 200 | 3.2 | 1:2 | 67.8 | 79.9 | 5.3 | 14.8 |
| 23 | 190 | 250 | 3.2 | 1:2 | 69.6 | 80.9 | 3.2 | 15.8 |

[a]JEFFERSOL EE and diethyl — molar ratio
[b]Selectivity on a lights-free basis
[c]<0.5% dioxane

I claim:

1. A method for the production of ethylene glycol dialkyl ethers of the formula ROCH$_2$CH$_2$OR, where R is a lower alkyl radical, comprising reacting a dialkyl ether of the formula ROR with an ethylene glycol monoalkyl ether of the formula ROCH$_2$CH$_2$OH, where R is defined as above, over a heterogeneous anionic ion exchange resin catalyst.

2. The method of claim 1 in which the reaction is carried out at a temperature in the range from about 100° to about 250° C. and at a pressure ranging from about 50 to about 500 psig.

3. The method of claim 1 in which R is defined as a methyl or ethyl radical.

4. The method of claim 1 in which the mole ratio of dialkyl ether to monoalkyl ether is in the range from about 1:1 to about 10:1.

5. A method for the production of ethylene glycol dialkyl ethers of the formula ROCH$_2$CH$_2$OR, where R is a methyl or ethyl radical, comprising reacting a dialkyl ether of the formula ROR with an ethylene glycol monoalkyl ether of the formula ROCH$_2$CH$_2$OH, where R is defined as above, over a heterogeneous anionic ion exchange resin catalyst.

6. The method of claim 5 in which the reaction is carried out at a temperature in the range from about 100° to about 250° C. and at a pressure ranging from about 50 to about 500 psig.

7. The method of claim 5 in which the mole ratio of dialkyl ether to monoalkyl ether is in the range from about 1:1 to about 10:1.

8. A method for the production of ethylene glycol dialkyl ethers of the formula $ROCH_2CH_2OR$, where R is a methyl or ethyl radical, comprising reacting dialkyl ether of the formula ROR with an ethylene glycol monoalkyl ether of the formula $ROCH_2CH_2OH$, where R is defined as above, in a mole ratio of dialkyl ether to monoalkyl ether from about 1:1 to about 10:1, over a heterogeneous anionic ion exchange resin catalyst at a temperature in the range from about 100° to about 250° C. and at a pressure ranging from about 50 to about 500 psig.

9. A method for the production of ethylene glycol dialkyl ethers of the formula $ROCH_2CH_2OR$, where R is a methyl or ethyl radical, comprising reacting dialkyl ether of the formula ROR with an ethylene glycol monoalkyl ether of the formula $ROCH_2CH_2OH$, where R is defined as above, in a mole ratio of dialkyl ether to monoalkyl ether of about 4:1, over a heterogeneous anionic ion exchange resin catalyst at a temperature in the range from about 150° to about 200° C. and at a pressure ranging from about 100 to about 500 psig.

* * * * *